United States Patent [19]

Zahradnik et al.

[11] 4,378,344

[45] Mar. 29, 1983

[54] METHOD AND APPARATUS FOR PERFORMING MULTIPLE, SIMULTANEOUS IN VITRO DIAGNOSTIC TESTS USING A SOLID PHASE SYSTEM

[75] Inventors: Richard J. Zahradnik, Scarborough; Roger N. Piasio, Yarmouth, both of Me.

[73] Assignee: Ventrex Laboratories, Inc., Portland, Me.

[21] Appl. No.: 80,106

[22] Filed: Sep. 28, 1979

[51] Int. Cl.³ .................... G01N 21/64; G01N 23/00; G01N 33/52; G01N 33/54; G01N 33/56; G01N 33/58

[52] U.S. Cl. .................... 436/500; 422/56; 422/58; 435/4; 435/7; 435/174; 436/531; 436/544; 436/810

[58] Field of Search .............. 424/1.5, 8, 12; 435/4, 435/7; 23/230 B; 422/56, 57, 58, 174

[56] References Cited

U.S. PATENT DOCUMENTS

| | | | |
|---|---|---|---|
| 3,464,798 | 9/1969 | Kiltha | 23/230 B X |
| 3,652,761 | 3/1972 | Weetall | 424/12 |
| 3,826,619 | 7/1974 | Bratu | 23/230 B X |
| 3,867,517 | 2/1975 | Ling | 424/1 |
| 3,879,262 | 4/1975 | Schuurs | 435/7 |
| 3,896,217 | 7/1975 | Johnson | 424/1 |
| 3,932,141 | 1/1976 | Beall | 424/12 X |
| 3,951,748 | 4/1976 | Devlin | 23/230 B X |
| 4,016,250 | 4/1977 | Saxena | 424/1 |
| 4,020,151 | 4/1977 | Bolz | 424/12 X |
| 4,066,512 | 1/1978 | Lai | 424/2 |
| 4,081,244 | 3/1978 | Rolita | 424/12 X |
| 4,092,408 | 5/1978 | Litt | 424/1 |
| 4,111,754 | 9/1978 | Park | 435/7 |
| 4,115,538 | 9/1978 | Satoh | 424/1 |
| 4,116,638 | 9/1978 | Kenoff | 424/1 |
| 4,135,884 | 1/1979 | Shen | 424/12 X |
| 4,146,602 | 3/1979 | Gutcho | 424/12 X |
| 4,197,287 | 4/1980 | Piasio | 424/12 X |
| 4,225,575 | 9/1980 | Piasio | 424/1 |

FOREIGN PATENT DOCUMENTS 2015158 9/1979 United Kingdom.

OTHER PUBLICATIONS

Smith, Biochem., vol. 14, No. 7, 1975, pp. 1496–1501.
Friedel, Clin. Chem., vol. 21, 1975, pp. 967–977.

*Primary Examiner*—Anna P. Fagelson
*Attorney, Agent, or Firm*—Irons & Sears

[57] ABSTRACT

A method for performing multiple, simultaneous in vitro diagnostic tests is provided. The method utilizes a solid phase device comprising a receptacle and an insert. The receptacle has one or more fixed components immobilized on its inner surface. The insert has one or more fixed components—different from those immobilized on the receptacle—immobilized on its surface which is in contact with a fluid sample when inserted therein. The test is performed by placing a fluid sample, having two or more mobile components reactive with the fixed components, into the receptacle and in contact with the insert for a period of time and measuring the changes which are a function of the concentration of the mobile components.

8 Claims, No Drawings

METHOD AND APPARATUS FOR PERFORMING MULTIPLE, SIMULTANEOUS IN VITRO DIAGNOSTIC TESTS USING A SOLID PHASE SYSTEM

BACKGROUND OF THE INVENTION

1. Field of the Invention

This invention relates to a method for performing multiple, simultaneous *in vitro* diagnostic assays using a solid phase system.

2. Description of the Prior Art

In recent years, numerous techniques have been employed in the area of laboratory diagnostics to simplify operating procedures of existing methods and to provide new methods of improved speed, sensitivity, and accuracy. In particular, solid phase reactions have been especially valuable in simplifying the manipulations of prior art procedures and making possible procedures that could not be performed with conventional homogeneous phase reactions.

A solid phase reaction is generally carried out between one reactant, the fixed component, immobilized on the surface of an insoluble support matrix, and a second reactant, the mobile component, in solution. The reaction occurs when a molecule or a molecular arrangement of the mobile reactant, in the course of diffusion, collides with a molecule of the fixed reactant immobilized on the surface of the solid support matrix. The reaction may be a conventional chemical reaction, a binding of the mobile component by the fixed component as in an immunochemical reaction between an antigen and an antibody, or it may be a binding of the mobile component by the fixed component accompanied by chemical transformation of one of the components such as occurs in an enzyme-catalyzed reaction. Quantitative results are obtained by measuring the formation of products or disappearance of reactants as in the case of conventional and enzyme-catalyzed reactions, and in measuring the amount of the mobile component bound or the amount of mobile component unbound, in the case of an immunochemical reaction.

Any conventional chemical reaction or enzyme-catalyzed reaction resulting in a directly or indirectly measurable change can, in principle, be carried out by solid phase techniques. Directly measurable changes include changes in pH, light absorbance in the visible and ultraviolet regions or changes in fluorescence intensity. Indirect measurements can be made whenever the primary reactants or products are not readily measurable themselves by interposing the action of a reagent to carry out further reaction steps resulting in a measurable change and by the introduction of specific separation techniques. Such strategies may be employed alone or in combination, as is understood in the art.

Where the reaction consists solely of binding, in the absence of chemical change, techniques developed in the field of immunochemistry may be used to measure the extent of the reaction. Solid phase reactions are especially suited for immunochemical assays because the reactants in bound form may readily be removed from the solution by virtue of their attachment to the solid phase. Frequently, however, the components bound in an immunochemical reaction cannot be directly measured because they are indistinguishable by chemical methods from other substances commonly present in the same reaction mixture, so that the mere disappearance of a reactive component from solution or its accumulation on the solid phase cannot be measured directly. Therefore, additional steps must be taken in order to make a measurable change related to the amount of binding.

The variety of approaches taken by workers in the prior art can be grouped into two general categories. In the first of these, termed competitive or indirect immunoassays, the immobilized component is present in controlled amount and the mobile component present in unknown amount. To the unknown amount of mobile component is added a known amount of the same component which has been tagged by the addition of a measurable substituent which does not interfere with its immunochemical reactive properties. The tag may consist of a radioisotope, a chromophore, a fluorophor or an enzyme. The amount of tagged material bound immuno-chemically to the solid phase will depend upon the amount of untagged component in solution competing for the same binding sites. The more of the unknown present, the less will be the amount of tagged component bound.

In the second general method, termed the sandwich method or direct method, the solid phase containing an amount of immunochemically bound mobile component resulting from the first immunochemical reaction is subjected to the action of a reagent which can also bind immunochemically to the solid phase, but only at sites already occupied by the immunochemically bound mobile component. The reagent may be tagged, for example, as in the first method with a radioisotope, a fluorophor, a chromophore or an enzyme. The amount of tagged reagent bound is a direct measure of the amount of mobile component bound, which, in turn, is a measure of the amount of mobile component initially present in the reaction mixture.

Where the tag is a radioisotope, the technique, whether competitive or noncompetitive, is termed a radioimmunoassay. When the tag is an enzyme, the assay is termed an enzyme-linked immunoassay. The amount of enzyme-tagged reactant is measured by any convenient method for measuring the activity of the enzyme used in the tag.

Other kinds of solid phase reactions of the type generally described hereinabove are presented by way of example. The immunoradiometric assay for quantitative determination of an antigen is conducted by first reacting a known excess of labeled antibody with the unknown amount of antigen in a homogeneous phase reaction. Subsequently, immobilized antigen in excess amount is added in order to bind the unreacted soluble labeled antibody. The amount of unknown antigen is determined by measuring the difference between the total labeled antibody and the amount bound to the solid phase. The method gives direct quantitative results only with an univalent antigen, i.e., antigen which can only bind one molecule of antibody.

In such solid phase technology, the reagent or reagents used in the procedure are usually immobilized by being coated or bonded, either covalently or by adsorption to the solid phase material, which is then immersed in the sample to be tested. The manner of coupling such reagents to the solid phase material is known. See, for example, the disclosures in U.S. Pat. Nos. 3,652,761, 3,879,262 and 3,896,217.

A solid phase immunological assay system is disclosed in Miles et al., "Properties of Two-Site Immunoradiometric (Labelled Antibody) Assay Systems", IAEA, 149 (1974) in which solid-phase antibodies were bound to a tube wall by an immunoglobulin "arm". Polystyrene tubes were coated with non-immune guinea pig immunoglobulin (GP.IgG) or rabbit-anti (GP.IgG) (R-anti(GP.IgG)), and immunoglobulin "spacer arms" of various lengths were built up by alternative reactions with GP.IgG and R-anti(GP.IgG) leaving a final coat of the latter. Antibodies specific to glial fibrillary acidic protein (GP-anti(GFAP)) and to ferritin (GP-anti (ferritin)) were then immunologically bound to the solid phase. This placed specific solid-phase antibody at various distances from the matrix. Increasing "arm" length was shown to improve the precision of the dose-response variable.

U.S. Pat. No. 4,081,244, issued Mar. 28, 1978 to Polito et al. discloses a method for the preparation of an immunochemical composite comprising an antibody bound through a diamino spacer molecule to a finely divided polysaccharide matrix using a bifunctional coupling agent. The antibody coupled to the spacer may be either a primary or a secondary antibody, although the latter is preferred.

In U.S. Pat. No. 4,092,408 issued to Litt on May 30, 1978, a solid-phase radioimmunoassay method is disclosed in which anti-antibody is adsorbed on a solid surface and antibody is then bound to the anti-antibody. This immobilized antibody is then employed in a radioimmunoassay of antigen.

Examples of commonly used solid phase materials include, but are not limited to, glass or polymeric tubes which are coated with the reagent or reagents on their internal surfaces; coated polymeric inserts; coated polymeric sticks as disclosed in copending application Ser. No. 905,552 of Piasio et al., filed May 15, 1978 now U.S. Pat. No. 4,225,575; micro and macro beads formed of polymers and of glass; porous matrices; coated membranes; and tablets.

Immunochemical assays are highly useful in clinical research and diagnosis. They are highly specific, owing to the highly selective nature of antigen-antibody reactions. The antigen-antibody binding is very tight so that once the binding reaction has had an opportunity to occur, the limit of detectability is determined by the measurability with which the tag can be detected. Immunochemical assays are exceedingly versatile, owing to the fact that they can be used to measure specific substances selectively against a background of chemically similar substances. Because of these desirable attributes, there has been considerable interest in improving the ease of manipulation, sensitivity, accuracy, speed and applicability of immunochemical assays. The development of solid phase immunoassays has been one of the major advances in the field.

Among the advantages of solid phase systems is that the reaction product or products can be separated from the reaction solution with relative ease, i.e., by physically removing the solid phase material. This is in contrast with a non-solid phase or a homogeneous reaction, which typically results in a homogeneous solution which requires more complex separation techniques.

The introduction of solid phase technology has permitted the performance of novel procedures that were heretofore extremely difficult using free solution technology. An example of this is the sandwich assay technique described hereinabove. While a sandwich assay is theoretically possible in a homogeneous solution, it is not desirable for practical reasons. The most important aspect which makes such assays impractical is the separation of the first antigen-antibody complex from a homogeneous phase solution requires the use of sophisticated physical-chemical techniques, especially if the antigen is relatively small compared to the antibody and molecular weight differences between free antibody and complexed antibody are slight. In contrast, the separation procedure in a solid phase system is a matter of the utmost simplicity.

The earliest solid phase systems devised were test tubes coated on the inside surface. Commercial examples of coated tube technology include the Immunotube TM system marketed by Smith Kline Instruments of Sunnyvale, Calif., and the Rianen TM system of New England Nuclear, North Billerica, Mass., and the tubes described in U.S. Pat. No. 3,867,517 issued Feb. 18, 1975 to Ling. Although coated tube systems have proven useful for immunoassay purposes, they fail to exploit the full range of potential advantages offered by solid phase systems. A principle disadvantage is that the surface-to-volume ratio is relatively low and reaction kinetics may be further hindered by the fact that the reactive surfaces are located at the boundary of the solution volume, which may be relatively remote from the main body of the solution. Therefore, the average distance between mobile reactants and reactive surfaces is large.

Attempts to improve on the performance of coated tubes have led to a variety of systems designed to increase the surface to volume ratio of the solid phase system. These methods have included providing highly convoluted surfaces, reducing the volume of liquid required and providing surfaces of finely divided material.

The SPAC TM system of Mallinckrodt Chemical Company is basically a coated tube system which exemplifies the strategy of providing a convoluted surface to increase surface area in the coated tube format. Additionally, the tubes are provided with a detachable lower section which may be batch coated to achieve greater uniformity from tube to tube.

A consequence of the batch immobilization on coated tube bottoms is that the outside as well as the insides of the tube become coated. This makes it difficult for the laboratory technician to work with the tubes without coming into contact with whatever materials are coated on their surface and valuable immunological reactants are wasted. The convoluted surface area is said to increase by three to four times the amount of reactive surface available. However, the reactive surface remains at the periphery of the solution, which may be suboptimal geometry from the standpoint of the average diffusion distance from the solution to the reactive surface. Due to the complexity of the surface, difficulties in washing the surface free of contaminating substances may be encountered. As with coated tube systems in general, the SPAC TM system is likely to be sensitive to convection currents which can result in large errors as previously described. Convection may be reduced by carrying out the reaction in a constant temperature bath. However, this procedure presents additional equipment requirements for the clinical laboratory. For measurement of hapten antigens, the system is additionally suboptimal if the reaction is carried out at 37° C. according to the manufacturer's recommendation. It has been shown that increasing the temperature of a certain antibody-hapten reaction tends to enhance the rate of dissociation of the antibody-hapten complex relative to the rate of its formation. See Smith, T. W., and Skubitz, K. M., *Biochemistry* 14, 1496 (1975) and Keave, P M., Walker, W. H. C., Gauldie, J. and Abraham, G. E., *Clinical Chemistry* 22, 70 (1976).

Various types of solid phase matrices designed to be inserted into the reaction fluid have been disclosed. A convoluted or sponge-like matrix designed to be inserted into the test solution is exemplified by U.S. Pat. No. 3,951,748, issued Apr. 20, 1976 to Devlin. This material offers relatively large surface areas but may be difficult to wash or drain thoroughly at the conclusion of the reaction. In addition, such systems may be limited in practice to the use of reactants and reagents which are readily eluted from the sponge matrix. More significantly, the sponge matrices tend to react extensively with only a portion of the reaction fluid, i.e., that portion which actually penetrates the pores of the matrix. Another solid phase matrix useful for assaying biologically active materials is disclosed in U.S. Pat. No. 4,066,512, issued Jan. 3, 1978 to Lai et al. This matrix comprises a microporous membrane, an inert proteinaceous material coated thereon, and a biologically active material immobilized onto this coating. This matrix can then be used for determining an unknown in a fluid sample.

A second type of insert, employing the strategy of forcing the reaction fluid to spread in a thin layer over the coated matrix surface, is disclosed in U.S. Pat. No. 3,826,619, issued July 30, 1974 to Bratu, et al., and U.S. Pat. No. 3,464,798, issued Sept. 2, 1969 to Kilthau. Both cases disclose a combination of a receptacle and closely-fitting insert matrix, so shaped as to squeeze the reaction fluid into a thin layer between the container walls and the matrix surface. The insert matrix must fit the container with a close tolerance, and the volume of reaction fluid must be carefully controlled, since variations could adversely affect the reproducibility of the assay. The apparatus of Bratu is designed for use in a direct immunochemical test that is qualitative only. Because the reaction solution is forced into a thin film by the insert, the reaction volume must necessarily be small and Bratu in fact discloses that the type of assay contemplated is designed for small volumes of undiluted serum. One of the pitfalls in this type of assay is that errors in the rates of antigen-antibody reactions may be caused by variations in the pH of undiluted serum, which may vary between pH 6 and pH 9 in clinical samples. The pH may be controlled by the addition of a buffer, but buffer salt concentrations greater than 0.1 M tend to dissociate antigen-antibody complexes. Therefore, an excess volume of low ionic strength buffer must be used to control pH accurately, and this may expand reaction volume to an unacceptable amount. Error due to the pH may be tolerated in a qualitative assay such as disclosed by Bratu et al., especially in samples relatively rich in concentration of unknown, but not in the quantitative assays for which the present invention is designed. Where diluting by buffer is required, a low concentration of unknown may be diluted below the level of detection, leading to false negative results with the Bratu or Kilthau device. A false negative result is one in which no unknown is detected when some should have been detected. One embodiment of the Bratu insert is an insert having four fins. Its use is disclosed for qualitative analysis where larger quantities of serum are available, but there is no suggestion of any different mode of operation from the thin film mode utilized with the rounded or conical version. The devices disclosed in U.S. Pat. No. 3,826,619 have not, so far is known, been commercially exploited.

An example of an insert which utilizes the "intimate contact" principle of Bratu and Kilthau, but is apparently used quantitatively, is disclosed in U.S. Pat. No. 4,135,884 issued Jan. 23, 1979 to Shen and represented by the "Gamma Stick ™ [$^{125}$I]T$_3$ Uptake Kit" of Alpha Gamma Labs, Inc., Sierra Madre, Calif. This insert has four flutes which are coated with an antigen or antibody and inserted into a test tube containing the unknown sample, in intimate contact with the sample.

A third type of solid phase insert matrix is represented by the StiQ ™ assay of International Diagnostic Technology Corporation, Santa Clara, Calif., designed to exploit a solid phase assay disclosed in U.S. Pat. No. 4,020,151, issued Apr. 26, 1977 to Bolz, et al. In this system, a disc shaped, uncoated insert matrix of material capable of adsorbing proteins from serum is provided. In this system, the limitations are not only due to surface-to-volume ratio or geometric considerations but are mainly due to problems associated with the initial adsorption step, such as the presence of interfering substances and the difficulty of obtaining measurable adsorption components present in low concentration.

Another example of an attempt to improve surface-to-volume ratio by reducing reaction volume is disclosed by Friedel, R. and Dwenger, A., *Clin. Chem.* 21, 967 (1975). In this system, capillary tubes are coated on the inside with a specific adsorbant and the reaction mixture is introduced into the lumen of the capillary tube.

A further example of such a device is disclosed in U.S. Pat. No. 4,111,754, issued Sept. 5, 1978 to Park which relates to a solid phase matrix having a cylindrical supporting surface with inwardly directing protuberations. The spacing between the protuberations is such that a liquid sample will be retained within the matrix by capillary action so that the sample can only be removed from the matrix by addition of another fluid on top of the matrix to build up a hydrostatic pressure head sufficient to overcome the capillary attraction. A further example of the continuing prior art trend toward maximizing surface to volume ratio and capillary devices is shown by U.S. Pat. No. 4,116,638 issued Sept. 26, 1978 to Kenoff. The Kenoff device consists of a bundle of capillary tubes contained in a holder designed to be inserted into a sample contained in a test tube.

One system which affords a high surface area for overall volume is the coated micro glass bead system as, for example, the Immo Phase ™ system of Corning Glass Works. This system exemplifies the use of finely divided particles. It provides a high coated surface area with a correspondingly high reaction rate. Due to settling of the particles during the reaction, optimization of test systems of this kind require that the test tubes in which they are placed during reaction be capped and mixed vertically during reaction to insure that all surfaces come in contact with the reactants. Further, the use of particles necessitates multiple centrifugations and washings to completely separate the immobilized product from the solution.

Another example of a system which affords high surface area for over-all volume is the coated macro bead as disclosed in U.S. Pat. No. 3,932,141, issued Jan. 13, 1976, to Beall et al. and represented by the AUSTRIA ™ II-125 and AUSAB ™ assays of Abbott Laboratories, North Chicago, Ill. This bead is designed so that a minimal amount of sample is required. It appears that the sample forms a thin film around the bead and as such would have the same deficiencies as described above for the Bratu device. This bead appears to be only useful for qualitative analysis and not for quantitative analysis.

Other examples of solid phase matrices, which alleviate many of the deficiencies of the prior art, are disclosed in copending patent application Ser. No. 805,431, filed June 10, 1977 of Piasio et al. and copending patent application Ser. No. 905,552 of Piasio et al., filed May 15, 1978. Application Ser. No. 805,431 discloses a water-insoluble solid phase matrix for insertion into a reaction vessel which comprises an elongated annular support surface and a plurality of water-insoluble fins projecting from the support surface. An antigen or an antibody capable of reacting with a mobile component in a liquid sample to be assayed is immobilized on the interior of the annular surface and on each of the fin surfaces. Application Ser. No. 905,552 now U.S. Pat. No. 4,225,475 discloses another water-insoluble solid phase matrix for insertion into a reaction vessel which comprises a handle having a plurality of essentially smooth curved or planar surfaces attached thereto which extend throughout the liquid sample being assayed. An antigen or an antibody is immobilized on the curved or planar surfaces which reacts with a mobile component in the liquid sample.

All of the above-described prior art is concerned with optimizing solid phase reactions by improvements in solid phase devices. None of the above-described prior art is concerned with solid phase systems for performing multiple, simultaneous diagnostic assays.

The first report of a multiple, simultaneous assay was by C. R. Morgan in *Proc. Soc. Exp. Biol. Med.* 123, 230 (1966). Morgan described a multiple, simultaneous radioimmunoassay for human growth hormone (HGH) and human insulin. In this competitive binding assay, anti-HGH and anti-insulin were utilized to bind HGH and insulin and $^{125}$I-HGH and $^{131}$I-insulin were utilized as the tracers. Soluble anti-antibody was used to precipitate the antigen-antibody complexes. The precipitate was then counted separately for $^{125}$I and $^{131}$I.

Similarly, F. Murad and A. G. Gilman described a simultaneous, competitive binding radioassay for cyclic AMP (cAMP) and cyclic GMP (cGMP). See *Biochim. Biophys. Acta* 252, 297 (1971). $^{3}$H-cGMP and $^{32}$P-cAMP and soluble protein binders, one specific for cAMP and the other specific for cGMP, were utilized for this assay. A cellulose ester filter was utilized to separate free from bound cAMP and cGMP. The filter was then counted separately for $^{3}$H and $^{32}$P. Similarly, R. E. Wehmenn, et al., *Endocrinology* 90, 330 (1972) discloses a simultaneous, competitive binding radioimmunoassay for cAMP and cGMP utilizing antibodies to cAMP and to cGMP and $^{125}$I-cGMP and $^{131}$I-cAMP as the tracers. Ammonium sulfate was used to precipitate the antigen-antibody complexes and the precipitate was counted separately for $^{125}$I and $^{131}$I.

In *Biochem. Biophys. Res. Comm.* 46, 2107 (1972), T. Mitsuma et al., describe a radioimmunoassay for thyroxine (T$_4$) and triiodothyronine (T$_3$) simultaneously. In this competitive binding assay, antibodies to T$_3$ and to T$_4$, $^{125}$I-T$_3$ and $^{131}$I-T$_4$ were utilized. A slurry of dextran-coated charcoal was used to separate the free from bound T$_3$ and T$_4$. The centrifuged charcoal was counted separately for the different labels. Following a similar procedure, V. Ledercq-Meyer, et al., *Diabetalogia* 11, 419 (1975) describe a simultaneous radioimmunoassay for glucagon and insulin; H. Tai and W. Y. Chey in *Anal. Biochem.* 74, 12 (1976) disclose a simultaneous radioimmunoassay for secretin and gastrin; and J.-G. Ljunggren et al., *Acta Endocrin.* 81, 187 (1976) disclose a simultaneous radioimmunoassay for T$_3$ and T$_4$.

U.S. Pat. No. 4,016,250 issued Apr. 5, 1977 to Saxena discloses a radioassay for human chorionic gonadotripin (HCG), luteinizing hormone (LH), prolactin (PRL) and other HCG-like material. The assay is a competitive binding assay using specific tissue receptors to bind the particular material assayed. The following radiolabels may be utilized in this process: $^{125}$I, $^{131}$I, $^{3}$H, $^{14}$C. This patent indicates that HGH and PRL or LH and PRL may be assayed simultaneously when different labels are used. The tissue receptors are centrifuged and counted separately for the different labels utilized.

Satoh et al., U.S. Pat. No. 4,115,538 which issued Sept. 19, 1978, disclose a competitive binding radioimmunoassay in which cAMP and cGMP are assayed simultaneously. $^{125}$I and $^{131}$I are utilized as the labels. Various procedures may be used to separate the free and bound cAMP and cGMP, such as, charcoal, ammonium sulfate, polyethylene glycol, or soluble anti-antibody. The separated fraction is counted separately for $^{125}$I and $^{131}$I.

A simultaneous radioassay for folate and vitamin B$_{12}$ is disclosed in U.S. Pat. No. 4,146,602, issued Mar. 27, 1979 to Gutcho and Mansbach. In this assay, folate labelled with $^{125}$I and B$_{12}$ labelled with $^{57}$Co are utilized as the tracers. Protein receptors or antibodies are used to bind the folate and B$_{12}$. Bound B$_{12}$ and folate are separated from the free form and counted separately for $^{125}$I and $^{57}$Co. This patent also postulates that the simultaneous radioassay may be effected using a solid phase assay technique whereby the receptors or antibodies for folate and B$_{12}$ are previously coated on or bound to a solid support, such as a test tube, or insoluble polymer. Thus, the bound and free portions may be readily separated. This patent does not indicate whether such an assay has been performed. Nor does it postulate performing a simultaneous assay using the same label.

Piasio et al. in copending application Ser. No. 905,552, described an apparatus useful for performing solid phase in vitro diagnostic tests. Two embodiments were discussed—one having a plurality of fins and a second having a plurality of rods. It was indicated in this application that such embodiments were adaptable to methods of carrying out several tests at one time by providing individual fins or rods with different coatings. However, although it is possible to do so, it is very impractical to coat individual fins or rods. As a result, applicants have developed the method of the present invention to perform multiple simultaneous in vitro diagnostic tests. This method utilizes a coated receptacle and a differently coated insert.

A process to perform multiple in vitro diagnostic tests simultaneously has at least the following advantages. Since several assays cam be performed on one assay sample rather than on several assay samples, a smaller total volume of a clinical sample is required to do an equivalent number of tests. This is important in clinical research and diagnosis where many assays have to be performed on a limited volume of a clinical sample. This is particularly important since an additional volume of a clinical sample is not readily available. Thus, it is best to be able to perform as many tests on the original sample as possible. In addition, by performing several assays at one time on a single assay sample, a smaller number of tubes have to be handled to complete the required number of tests. This makes the performance of all the tests more efficient and enables the technician to perform in vitro diagnostic tests on more clinical samples than previously possible. Applicants have developed a method whereby several in vitro diagnostic tests can be conducted simultaneously even if the same means of measurement is used for each of several of the individual assays conducted in the overall, multiple test.

SUMMARY OF THE INVENTION

The disadvantages of the prior art have been alleviated by the present invention. In accordance with the present invention, a method is provided for conducting multiple in vitro diagnostic tests in which two or more reactants, each termed a fixed component, is attached to solid phase matrix comprising a receptacle and an insert and two or more other reactants, each termed a mobile component, is dispersed in a liquid medium in which the matrix is brought into contact therewith. In particular, at least one fixed reactant is attached to an insert which may be immersed in the liquid and at least one different fixed reactant is attached to a receptacle in which the fluid is placed. The method comprises conducting several tests simultaneoulsy using a coated insert and a differently coated receptacle.

The shape of the insert is designed to provide an optimal surface-to-volume ratio and a shorter average diffusion distance between the mobile reactants in solution and the fixed reactants on the solid phase surfaces of the insert and receptacle, and also to permit the liquid to drain freely from the insert and receptacle when the liquid is poured therefrom. The insert of the present invention may comprise any insertable solid phase matrix known in the art, e.g., beads, membranes, tablets or polymeric inserts. However, it is preferred to use a stick as described in copending application Ser. No. 905,552 having at least nine fins. This nine-fin stick comprises a plurality of essentially smooth or curved planar surfaces attached to a supporting member which are of a size and shape and are arranged in such a fashion with respect to the reaction fluid that the insertion of the stick in the fluid reduces the average diffusion distance of the mobile component molecules to the stick surface compared to the average diffusion distance to the inner surface of the receptacle when no insert is present. The actual shape of a given finned stick, may, but need not, be designed to conform to the size and shape of the receptacle into which it is placed. However, the finned stick matrix must extend substantially through the depth of the fluid sample in the vessel. In some systems, these finned stick matrix surfaces preferably extend above the surface of the reaction fluid thereby producing an essentially constant geometric relationship through the depth of the reaction fluid and further providing that the same geometric relationship will exist regardless of any changes in the fluid volume.

The receptacle, according to this invention, is also a solid phase matrix into which the insert is placed. Through the use of this receptacle, preferably a test tube, an additional solid phase matrix is provided on which a coating different from that on the insert may be applied. The solid phase matrix on the receptacle must extend substantially throughout the depth of the fluid sample in the vessel, regardless of the type of insert used. Also, in some systems, the solid phase matrix preferably extends above the surface of the reaction fluid, thereby producing essentially constant geometric relationship throughout the depth of the reaction fluid and further providing that the same geometric relationship will exist, regardless of any changes in the fluid volume.

In the preferred embodiment of the present invention, where a coated tube and coated nine fin insertable matrix are employed together, an immunological spacer consisting of immunoglobulin G (IgG) is adsorbed on the surfaces of both the insertable matrix and the receptacle. An anti-antibody is then immunologically bound to the IgG. The matrix can then be used as a solid phase anti-antibody in any immunological antibody-antigen assay employing a primary antibody. Alternatively, the solid phase anti-antibody could be allowed to react with a solution containing only primary antibody and the resulting solid phase antibody used in a direct or indirect immunoassay for antigen.

Advantages of the invention include the minimization of the number of tubes required for conducting several tests since the tests may all be conducted in one tube. This makes the procedure more afficient. By performing several tests at one time, it is possible to increase the number of clinical samples which may be assayed in any given time interval. Additionally, since several tests can be performed on a single assay volume, less total volume of a clinical sample is required for conducting all of the tests which is important since an additional volume of a clinical sample is not readily available if it were to be required. Another advantage of the invention is the separability of the insert and receptacle. This allows a smaller number of labels to be used for the multiple assay procedure.

DESCRIPTION OF THE PREFERRED EMBODIMENTS

In the method of the present invention, solid phase reactions are carried out in a receptacle having one or more of the reaction components bound to its surface and using an insert which is placed into the reaction fluid in the receptacle and having one or more reaction components, different from those on the receptacle, bound to its surface. The improvement of the present invention over the prior art solid phase assays is that several different assays may be conducted simultaneously on the same fluid sample. This is accomplished by using a receptacle and an insert each having different coatings. By utilizing a coated receptacle and a differently coated insert, it is possible to conduct a simultaneous assay even if the identical label is used for each tag in each individual assay. This is possible because the receptacle and insert can be separated prior to measurement. Through the use of different labels, it is possible to conduct several more assays simultaneously. Preferably, the reaction components bound to these surfaces are bound by means of an immunological spacer and an anti-antibody. For purposes of illustration, reactions carried out in test tubes are described and a stick as described in copending application Ser. No. 905,552 having at least nine fins and designed to be inserted into the test tubes are discussed. The reaction is readily initiated by adding the mobile component into the tube which contains a solid phase coating and inserting the solid phase coated stick into the tube. The reaction may be terminated by draining the fluid from the tube. After the reaction has been terminated, the tube and stick may be placed in a radioactivity counting chamber or other measurement device, depending upon the nature of the assay method.

One disadvantage of prior art simultaneous assays is the requirement that different labels, e.g. $^{125}$I and $^{131}$I, must be used in order to obtain correct measurements. The present invention alleviates this disadvantage. By utilizing a receptacle having one coating and an insert having a different coating, it is possible to separate the receptacle and the insert for measurement purposes. Thus, it is now possible to conduct a simultaneous solid phase assay in which the identical label may be used for each tag. Any label known in the art may be utilized to label the tags. Several examples of different labels include: radiolabels, enzymes, fluorophors or chromophors. For example, in a solid phase radioimmunoassay for triiodothyionine ($T_3$) and thyroxin ($T_4$), the receptacle could be coated with anti-$T_3$ and the insert with anti-$T_4$. Since the insert and receptacle are separable, $^{125}$I-$T_3$ and $^{125}$I-$T_4$ can be utilized as the tags.

In accordance with the present invention, it is also possible to coat more than one fixed component on the receptacle and insert. Thus, for example, by mixing together several different antibodies and then coating the receptacle or insert, it is possible to coat more than one antibody on the receptacle or insert. In the case where several fixed components are coated on the same solid phase, it is necessary that different labels be utilized. The coating of more than one fixed component on each surface permits the simultaneous assaying of more than two mobile components. For example, if $^{125}$I-$T_3$ and $^{131}$I-$T_4$ are used as the tags, anti-$T_3$ and anti-$T_4$ could then be coated on the receptacle. Then if $^{125}$I-insulin and $^{131}$I-glucagon are used as tags, anti-insulin and anti-glucagon could be coated on the insert. Thus, the same set of labels, i.e. $^{125}$I and $^{131}$I, may be used in the measurement of the mobile components reactive with the fixed components on the receptacle and in the measurement of the mobile components reactive with the fixed components on the insert. This combination would then permit the assaying of four unknowns simultaneously in one assay volume. It would also permit the use of only two labels to assay the four unknowns. Thus, one advantage of the present invention is that a smaller member of labels, e.g. radiolabels, enzymes, etc., is required. This simplifies the measurement step since there are fewer different labels to measure. Another advantage of the present invention is that a smaller total volume of a clinical sample is required to conduct an equivalent number of tests. Also, since less tubes are needed to conduct the simultaneous assays, the assays are more efficient, and hence many more can be completed in a given time interval.

It will be appreciated that design of a properly functional solid phase matrix requires attention to all aspects and variables affecting the reaction to be conducted. In addition to providing a structural basis for enhanced reaction rates, operating convenience, minimized background interference and all the other advantages of the present invention, it is important to provide a coated surface having immobilized reactant distributed therein in such a manner that its reactivity is maximum. The immobilized component should be distributed as uniformly as possible over the surface. Gaps in the coating, which may be caused, for example, by an air bubble lodged on the matrix surface during the coating step, must be avoided. The immobilized reactant molecules must be exposed on the matrix surface, not buried in excess reactant or other carrier matter. Preferably, the immobilized reactant should be bound to the matrix sufficiently strongly that no appreciable amount of reactant becomes desorbed, or otherwise removed during the incubation or washing steps of the reaction. In accordance with the preferred embodiment, the reaction component is accessible because it is immunologically bound to an anti-antibody which in turn is immunologically bound to an immunological spacer which is adsorbed to the surfaces of the matrices.

In accordance with the present invention, a simultaneous assay is conducted in a receptacle having one coating and utilizing an insert having a different coating. The coating on the receptacle and insert are different. When two assays are to be conducted simultaneously, the fixed component for one will be coated on the receptacle and the fixed component for the other will be coated on the insert. It is possible to use the same label in this simultaneous assay system since the insert and receptacle are separable and can therefore be measured separately. If it is desired to conduct more than two assays simultaneously, one or more different fixed components may be coated on the receptacle and two or more different fixed components—also different from those coated on the receptacle—may be coated on the insert. When two or more different fixed components are coated on the insert or receptacle, different labels must be used for the measurement of each of the mobile components reactive with the fixed components on the same surface. For example, a simultaneous assay for three unknowns may be performed by using a receptacle having one fixed component immobilized thereon and an insert having two different components immobilized thereon. The label for the assay using the fixed component on the receptacle and the label for one of the assays using the fixed components on the insert may be identical. The labels for the two assays using the fixed components on the insert must be different. An example of this would be a simultaneous assay for human chorionic gonadotropin (HCG), prolactin (PRL) and luteinizing hormone (LH). Anti-LH could be coated on the receptacle and both anti-HCG and anti-PRL could be coated on the insert. $^{125}$I-LH, $^{125}$I-HCG and $^{131}$I-PRL could then be used as tags. Since only two different labels are used, only two channels would be required for the measurement of the labels. Thus, it is possible to simultaneously assay for many unknowns in one assay volume using a minimum number of labels.

Preferably, a coated test tube is utilized as the receptacle, although coated beakers and the like could also be used. Although coated beakers and the like may be utilized as the receptacle, they may be impractical for certain of the inserts. For example, the principle behind the close-fitting inserts and macro beads is intimate contact with the fluid sample. This intimate contact would be difficult to achieve if a coated beaker were used but easily achievable if a coated test tube were used. Coated beakers and the like may also require a larger volume of the clinical sample which would make them less desirable to use.

The insert may be any conventional solid phase matrix which can be inserted into the receptacle. Examples of suitable matrices include: polymeric inserts, micro beads, macro beads, coated membranes, tablets, close-fitting inserts as described by Bratu et al., Kilthau, or Shen or sticks as disclosed in copending application Ser. No. 905,552. Although any conventional insertable solid phase matrix can be used for a multiple, simultaneous assay for two unknowns, it may be impractical to use several of them when assaying for three or more unknowns. For example, it may be impracticle to coat two or more different fixed components on the inserts operating under the principle of intimate contact such as, the close fitting inserts or macro beads. While such an assay is feasible, it may not be very efficient. Thus, it is preferred to use as the coated insert a stick having at least nine fins as described in copending application Ser. No. 905,552, incorporated herein by reference.

The tube and insert may be coated using any method known in the art. In the preferred embodiment, an immunological spacer is adsorbed onto the inner surface of the tube and onto the surface of the insert which is in contact with the fluid sample when inserted therein. An anti-antibody is then immunologically bound to said spacer. The tube and insert coated in this manner can then be used as a solid phase anti-antibody in any immunological antibody-antigen assay employing a primary antibody. Alternatively, an antibody could be immunologically bound to the solid phase anti-antibody. This solid phase antibody could then be used in a direct or indirect immunoassay for antigen.

A more complete appreciation of the invention will be realized by reference to the following specific examples. These examples are not intended to limit the invention disclosed herein except to the extent to which limitations appear in the appended claims.

In the following examples, all radioactivity counts were measured at 48% efficiency. In the following examples, the nine fin stick refers to a stick which is made in accordance with copending application Ser. No. 905,552 having nine fins.

EXAMPLE 1

This example describes the immobilizing of antibodies to a tube and a preferred nine fin stick.

The antibodies and anti-antibodies are prepared in the conventional manner. Thus, an antibody may be prepared by injecting an antigen into a rabbit. Rabbit immunoglobulin G (IgG) is injected into a second animal, e.g., a goat, to prepare goat antirabbit anti-antibody. This anti-antibody will bind any antibody produced in rabbits. In this particular example, rabbit immunoglobulin G will be the most suitable immunological spacer.

$12 \times 75$ mm commercially available polystyrene tubes were utilized. These tubes and 9-fin sticks as described in copending application Ser. No. 905,552 were coated with 1.4 ml of Rivanol fractionated rabbit IgG containing 10–20 $\mu$g of IgG/ml. Coating was performed in the standard fashion employing a buffer of pH 7.5 containing 0.01 M phosphate, 0.15 M NaCl and 1 mg/ml NaN$_3$. The coating reaction was performed for 18 hours at 5°–9° C. The tubes and sticks were then washed.

Goat antirabbit anti-antibody was then immunologically bound to the IgG coated tubes and sticks. 10 $\mu$g of goat IgG containing 10–30% anti-antibody/1.4 ml of the same buffer was used for this step which was performed for a minimum of 18 hours at room temperature. The tubes and sticks were then washed and air dried.

The anti-antibody coated tubes and sticks were then ready to immunologically bind specific antibody produced in rabbits. For example, rabbit anti-digoxin was bound to the anti-antibody in a similar manner. The anti-digoxin in buffer was immunologically reacted with the anti-antibody coated tubes and sticks for 24 hours at room temperature. The tubes and sticks were washed and air dried. They were then ready to be used in an immunoassay to determine the amount of digoxin in the fluid sample. The final coating procedure could utilize any rabbit antibody.

EXAMPLE 2

This example describes the immobilizing of two antibodies to sticks using rabbit anti-digoxin and rabbit anti-thyroxin as the antibodies.

Nine fin sticks were coated with IgG and anti-antibody as described in Example 1. Anti-digoxin and anti-thyroxin were mixed prior to coating the anti-antibody coated sticks. These two antibodies were then immunologically bound to the anti-antibody coated sticks using the same buffer and for a period of 24 hours at room temperature. The sticks were then washed and dried after which they could be utilized to determine the amount of digoxin and thyroxin in a fluid sample.

EXAMPLE 3

This example demonstrates that there is no significant difference in the binding of an antigen to its antibody which is coated on a tube when there is (1) not any stick, (2) an uncoated stick, or (3) a stick coated with a different antibody present in the reaction system. Two series were conducted for this example. In one, anti-digoxin was coated on the tube and anti-thyroxin on the stick. In the other, anti-thyroxin was coated on the tube and anti-digoxin on the stick.

Tubes and 9-fin sticks were coated with IgG, anti-antibody and antibody as described in Example 1. For purpose of illustration the assay for digoxin will be described. The following reactants were added to tubes having an anti-digoxin coating: 1.2 ml of 0.01 M phosphate-buffered saline (PBS) composed of 0.002 M NaH$_2$PO$_4$, 0.008 M Na$_2$HPO$_4$, 0.15 M NaCl and 0.1% bovine serum albumin at pH 7.4; 50 $\mu$l of standard digoxin containing 0, 0.5, 1.0, 2.0, 4.0, or 6.0 ug of digoxin; and 100 $\mu$l of $^{125}$I-digoxin. An uncoated stick or a stick coated with anti-T$_4$ were placed in several of the tubes containing the assay medium. The reaction was conducted for 1 hour at room temperature and then stopped by decanting the tubes. The percent of $^{125}$I-digoxin bound to the tube was then determined.

Table 1 shows the percent binding of $^{125}$I-digoxin to anti-digoxin coated tubes with (1) no stick, (2) an uncoated stick or (3) a stick coated with anti-T$_4$ present.

Table 2 shows the percent binding of $^{125}$I-T$_4$ to anti-T$_4$ coated tubes with (1) no stick, (2) an uncoated stick or (3) a stick coated with anti-digoxin present.

TABLE 1

| | % Binding of $^{125}$I-Digoxin | | | | | | |
|---|---|---|---|---|---|---|---|
| | 0 | 0.5 | 1.0 | 2.0 | 4.0 | 6.0 | ($\mu$g Digoxin) |
| 1 | 36 | 33 | 30 | 24 | 16 | 12 | |
| 2 | 37 | | | | | | |
| 3 | 37 | 33 | 28 | 23 | 16 | 12 | |

TABLE 2

| | % Binding of $^{125}$I-T$_4$ | | | | | |
|---|---|---|---|---|---|---|
| | 0 | 2.5 | 5.0 | 10.0 | 25.0 | ($\mu$g T$_4$) |
| 1 | 36 | 29 | 23 | 16 | 8 | |
| 2 | 31 | | | | | |
| 3 | 30 | 25 | 20 | 15 | 7 | |

The values for (2) and (3) in Table 2 are slightly, although not significantly lower, probably as a result of the displacement of the fluid above the coated portion of the tube when the stick was inserted. The values probably would have been as close as in Table 1 if this had not occurred. This example shows that there is no significant difference in the amount of binding of antigen to antibody coated on a tube when a coated stick is also present.

EXAMPLE 4

This example demonstrates that there is no significant difference in the binding of an antigen to its antibody which is coated on a stick when (1) an uncoated tube or (2) a tube coated with a different antibody is present in the reaction system.

Tubes and 9-fin sticks were coated with Ig6, anti-antibody and antibody as described in Example 1. The reactants utilized were those as described in Example 3. The reactants including $^{125}$I-digoxin were added to (1) uncoated tubes or (2) anti-T$_4$ coated tubes. Anti-digoxin coated sticks were then inserted and the reaction conducted for 1 hour at room temperature. The percent of $^{125}$I-digoxin bound to the stick was then determined. Table 3 shows the results of this example.

TABLE 3

| | % Binding of $^{125}$I-Digoxin | | | | | |
|---|---|---|---|---|---|---|
| | 0 | 0.5 | 1.0 | 2.0 | 4.0 | 6.0 | (μg Digoxin) |
| 1 | 54 | 43 | 38 | 30 | 18 | 14 |
| 2 | 45 | 38 | 33 | 28 | 16 | 12 |

This example shows that there is no significant difference in the amount of binding of antigen to its antibody coated on a stick when a coated tube is also present.

EXAMPLE 5

This example shows that there is no significant difference in the amount of binding of an antigen to a stick which is coated with different antibodies one of which is specific for the antigen.

Nine fin sticks were coated with (1) anti-T$_4$ as described in Example 1 and (2) anti-digoxin and anti-T$_4$ as described in Example 2. The following reactants were added to uncoated tubes: 1.1 ml of PBS buffer, 50 μl of digoxin standard, 50 μl of T$_4$ standard and 100 μl of $^{125}$I-T$_4$. A stick coated with (1) anti-T$_4$ and (2) anti-digoxin and anti-T$_4$ were inserted in the tubes. The reaction was conducted for 1 hour at room temperature. The percent of $^{125}$I-T$_4$ bound to the sticks were then determined. The results are shown in Table 4.

TABLE 4

| | % Binding of $^{125}$I-T$_4$ | | | | |
|---|---|---|---|---|---|
| | 0 | 2.5 | 5.0 | 10.0 | 25.0 | (μg T$_4$) |
| 1 | 56 | 37 | 24 | 15 | 7 |
| 2 | 55 | 35 | 26 | 14 | 8 |

This example shows that there is no significant difference in the amount of binding of an antigen to an antibody coated stick which contains multiple antibodies.

EXAMPLE 6

This example shows that a simultaneous assay can be conducted for at least two antigens on a single fluid sample.

Tubes and 9-fin sticks were coated with IgG, anti-antibody and antibody as described in Example 1. Digoxin and thyroxin were utilized as the antigens. 1.1 ml of 0.01 M PBS at pH 7.4 and also containing 5 mg/ml thimersol was added to the appropriate tubes. 50 μl of a digoxin solution and 50 μl of a T$_4$ solution were added to each tube. 100 μl of $^{125}$I-Digoxin, $^{125}$I-T$_4$ or 100 μl of the PBS buffer were added to the appropriate tubes resulting in a total volume of 1.4 ml. The sticks were inserted and the reaction conducted for 1 hour at room temperature. Table 5 shows the composition of each tube excluding the 1.1 ml of PBS buffer.

TABLE 5

| Tube | Digoxin std. (ng/ml) | Thyroxin std. (ng/ml) | $^{125}$I-Digoxin | $^{125}$I-Thyroxin | Buffer |
|---|---|---|---|---|---|
| 1 | 0 | 0 | 100 (μl) | — | 100 (μl) |
| 2 | 0 | 0 | — | 100 (μl) | 100 |
| 3 | 0 | 0 | 100 | 100 | — |
| 4 | 0 | 30 | 100 | — | 100 |
| 5 | 0 | 30 | — | 100 | 100 |
| 6 | 0 | 30 | 100 | 100 | — |
| 7 | 4 | 0 | 100 | — | 100 |
| 8 | 4 | 0 | — | 100 | 100 |
| 9 | 4 | 0 | 100 | 100 | — |
| 10 | 4 | 30 | 100 | — | 100 |
| 11 | 4 | 30 | — | 100 | 100 |
| 12 | 4 | 30 | 100 | 100 | — |

The following series of assays were conducted.
(A) anti-digoxin coated tube;
(B) uncoated tube and anti-T$_4$ coated stick
(C) anti-digoxin coated tube and uncoated stick; and,
(D) anti-digoxin coated tube and anti-T$_4$ coated stick.

Table 6 shows the results of this experiment. In this table, the amount of $^{125}$I-digoxin which bound to the coated tube when 0 ng/ml of digoxin standard was present is expressed as 100%. Similarly the amount of $^{125}$I-T$_4$ which bound to the coated stick when 0 ng/ml of T$_4$ standard was present is expressed as 100%. The remainder of the values are based on these two values.

TABLE 6

| | % $^{125}$I-Digoxin Bound | | |
|---|---|---|---|
| Tube | A | C | D |
| 1 | 100 | 118 | 126 |
| 3 | 98 | 109 | 121 |
| 4 | 97 | 111 | 109 |
| 6 | 100 | 104 | 110 |
| 7 | 66 | 76 | 68 |
| 9 | 69 | 77 | 70 |
| 10 | 62 | 76 | 69 |
| 12 | 63 | 73 | 68 |

| | % $^{125}$I-Thyroxin Bound | |
|---|---|---|
| Stick | B | D |
| 2 | 100 | 96 |
| 3 | 106 | 106 |
| 8 | 101 | 100 |
| 9 | 113 | 108 |
| 5 | 81 | 79 |
| 6 | 92 | 95 |
| 11 | 82 | 81 |
| 12 | 92 | 89 |

This table shows that there is no significant difference in digoxin binding to the anti-digoxin coated tube when T$_4$, $^{125}$I-T$_4$ or both are present in the assay mixture. Similarly, no significant difference in T$_4$ binding to the anti-T$_4$ coated stick is seen when digoxin, $^{125}$I-digoxin or both are present in the assay mixture. This experiment also demonstrates that there is no significant difference in digoxin binding to the anti-digoxin coated tube when an uncoated stick or an anti-T$_4$ coated stick is also present. Similarly, no significant difference in T$_4$ binding to the anti-T$_4$ coated stick is seen when an anti-digoxin coated tube is also present. All of this shows that it is possible to conduct an assay for at least two antigens simultaneously even when the label is the same.

EXAMPLE 7

This example shows that a simultaneous assay can be conducted for at least two antigens in a clinical serum sample.

Tubes an 9-fin sticks were coated with IgG, anti-antibody and antibody as described in Example 1. The basic procedure of Example 6 was followed for this example with the composition of each tube as shown in Table 7.

TABLE 7

| Tube | Clinical Sample (μl) | $^{125}$I-Digoxin (μl) | $^{125}$I-Tyroxin (μl) | Buffer (μl) |
|---|---|---|---|---|
| 1 | 100 | 100 | — | 100 |
| 2 | 100 | — | 100 | 100 |
| 3 | 100 | 100 | 100 | — |

The same series of assays were conducted as described in Example 6 and expressed in the same manner. Table 8 shows the results of this experiment.

TABLE 8

| | % $^{125}$I-Digoxin Bound | | |
|---|---|---|---|
| Tube | A | C | D |
| 1 | 100 | 95 | 114 |
| 3 | 98 | 135 | 116 |

| | % $^{125}$I-Thyroxin Bound | |
|---|---|---|
| Stick | B | D |
| 2 | 100 | 102 |
| 3 | 146 | 143 |

This table shows the same pattern of results as discussed in Example 6.

By preparing a standard curve for digoxin and thyroxin utilizing an anti-digoxin coated tube and an anti-thyroxin coated stick, the amount of digoxin and thyroxin in a clinical sample can be determined.

What is claimed is:

1. A method for simultaneously assaying a fluid sample for at least two different unknown mobile components contained therein which method comprises:
   (a) placing said fluid sample inside a receptacle having immobilized on its inner surface at least one fixed component reactive with at least one mobile component of the fluid sample and also containing a solid coated insert so positioned as to contact said fluid sample, which coated insert has immobilized on its surface in contact with said fluid sample at least one fixed component which is different from any fixed component immobilized on the inner surface of said receptacle and is reactive with at least one of the mobile components of the fluid sample that is unreactive with any fixed component immobilized on the inner surface of said receptacle,
   (b) allowing the mobile components of the fluid sample to react with the fixed components immobilized on the receptacle inner surface and on that surface of the solid insert in contact with the sample for a predetermined time period and,
   (c) determining the concentration of each reactive mobile component originally present in said fluid sample based on the amount of each of said reactive mobile components that reacted with each of said reactive fixed components during said predetermined time period.

2. The method of claim 1 in which the entirety of either the fixed component or the mobile component of each fixed component-mobile component reactive pair is labelled prior to placing said sample in said receptacle.

3. The method of claim 2 in which each of the reactive pairs is labelled with the same label.

4. The method of claim 2 in which each of the reactive pairs is labelled with a different label.

5. The method of claim 2 wherein each of the mobile components is an antigen, each of the fixed components is an antibody specific for one of said antigens and each reaction is a binding reaction of antigen to antibody.

6. The method of claim 2 in which each of said fixed components comprises an anti-antibody to which is immunologically bound an antibody to said anti-antibody, which antibody is also specifically reactive with an antigen of the fluid sample.

7. The method of claim 2 wherein said insert comprises a central rod with at least nine fin-like projections extending outwardly from said rod along a portion of the length of said rod and the receptacle is a test tube.

8. An apparatus for conducting in vitro immunoassays in accordance with claim 5 or 6 which comprises a receptacle having immobilized on its inner surface at least one fixed immunological component and a solid coated insert having immobilized on its surface at least one fixed immunological component different from and unreactive with any fixed component immobilized on the inner surface of said receptacle.

* * * * *